(12) United States Patent
Balsdon et al.

(10) Patent No.: US 9,310,349 B2
(45) Date of Patent: Apr. 12, 2016

(54) SENSOR STRUCTURE FOR EVAP HYDROCARBON CONCENTRATION AND FLOW RATE

(71) Applicant: Continental Automotive Systems, Inc., Auburn Hills, MI (US)

(72) Inventors: David William Balsdon, Chatham (CA); Brian Gordon Woods, Chatham (CA)

(73) Assignee: Continental Automotive Systems, Inc., Auburn Hills, MI (US)

( * ) Notice: Subject to any disclaimer, the term of this patent is extended or adjusted under 35 U.S.C. 154(b) by 279 days.

(21) Appl. No.: 14/101,387

(22) Filed: Dec. 10, 2013

(65) Prior Publication Data

US 2015/0160180 A1 Jun. 11, 2015

(51) Int. Cl.
| | |
|---|---|
| *F02M 25/08* | (2006.01) |
| *G01N 33/22* | (2006.01) |
| *G01N 7/00* | (2006.01) |
| *G01N 25/00* | (2006.01) |
| *G01N 29/02* | (2006.01) |
| *G01N 29/024* | (2006.01) |
| *G01F 1/42* | (2006.01) |
| *G01F 1/74* | (2006.01) |
| *F02D 41/00* | (2006.01) |
| *G01N 15/00* | (2006.01) |
| *G01N 15/06* | (2006.01) |

(52) U.S. Cl.
CPC .......... *G01N 33/225* (2013.01); *F02D 41/0045* (2013.01); *F02M 25/08* (2013.01); *G01F 1/42* (2013.01); *G01F 1/74* (2013.01); *G01N 7/00* (2013.01); *G01N 25/00* (2013.01); *G01N 29/02* (2013.01); *G01N 29/024* (2013.01); *F02D 41/0042* (2013.01); *G01N 15/06* (2013.01); *G01N 2015/0007* (2013.01); *G01N 2291/02809* (2013.01); *G01N 2291/02836* (2013.01)

(58) Field of Classification Search
CPC .............. F02M 25/08; F02M 25/0818; F02M 25/0836; F02M 25/089; F02M 31/18; F02M 33/04; F02M 2025/0881; F02M 35/10144; F02M 35/10157; F02M 35/10255; G01L 1/00; G01L 1/18; G01L 1/22; G01N 7/00; G01N 25/00; G01N 27/12; G01N 27/125; G01N 29/02; G01N 33/225
USPC ............. 123/516–521; 73/19.01, 23.2, 29.01, 73/23.31, 23.33, 114.38, 114.39
See application file for complete search history.

(56) References Cited

U.S. PATENT DOCUMENTS 5,188,085 A 2/1993 Habaguchi et al.
5,992,395 A * 11/1999 Hartsell, Jr. ...... B60K 15/03504
123/516

(Continued)

FOREIGN PATENT DOCUMENTS

DE 19509310 A1 9/1996
DE 102010040396 A1 3/2012

OTHER PUBLICATIONS

DE 19509310 A1 English Machine Translation.

*Primary Examiner* — John Kwon
*Assistant Examiner* — Johnny H Hoang

(57) ABSTRACT

A system and method controls a ratio of fuel to gas delivered to an internal combustion engine. Fuel for the engine is stored in a fuel supply. The fuel supply generates fuel vapor that is retained in a canister. The canister is in fluid communication with the engine via a flow path. Hydrocarbon concentration of fuel vapor in the flow path is determined. Pressure drop across a restrictive orifice provided in the flow path is measured to determine a flow rate of the fuel vapor in the flow path. A flow of the fuel vapor through the flow path and to the engine is controlled and injection valves that inject fuel into the engine are controlled so that an amount of fuel injected into the engine is based on the determined concentration of hydrocarbons in the fuel vapor.

15 Claims, 3 Drawing Sheets

(56) References Cited

U.S. PATENT DOCUMENTS

| | | | |
|---|---|---|---|
| 7,320,315 B2* | 1/2008 | Amano | F01M 13/023 123/357 |
| 8,312,868 B2 | 11/2012 | Bierl et al. | |
| 2004/0035219 A1* | 2/2004 | Moriyama | G01F 1/704 73/861.42 |
| 2011/0283774 A1* | 11/2011 | Sekiya | G01N 27/4077 73/30.01 |
| 2012/0055263 A1 | 3/2012 | Konzelmann | |
| 2013/0152905 A1 | 6/2013 | Woods et al. | |
| 2014/0238116 A1* | 8/2014 | Kwan | G01F 1/667 73/61.79 |

* cited by examiner

US 9,310,349 B2

SENSOR STRUCTURE FOR EVAP HYDROCARBON CONCENTRATION AND FLOW RATE

FIELD

This invention relates to vapor management systems of vehicles and, more particularly, to a system that includes sensor structure for monitoring hydrocarbon concentration and flow rate of a gas flow to control an air/fuel ratio of an engine.

BACKGROUND

Conventional gasoline engines of automobiles not only emit pollutant emissions via combustion of fuel or via emission of lubricant or fuel in the crankcase, the engines also produces hydrocarbon emissions via evaporation of fuel stored in the automobile. To reduce or eliminate this form of emission, modern automobiles store the fuel vapor in a canister and control its release from the canister into the combustion chamber for combustion. With reference to FIG. 1 such on-board evaporative emission control system (EVAP), generally indicated at 10, typically includes a fuel vapor collection canister (e.g., a carbon canister) 12 and a normally closed canister purge valve 14 connected between a fuel tank 16 and an intake manifold 18 of an internal combustion engine 20 in a known fashion. A normally open canister vent valve 22 is in fluid communication between a vapor collection canister 12 and ambient atmospheric conditions via a filter 24. Under certain conditions, the purge valve 14 is opened to direct hydrocarbon vapors to the intake manifold 18 to be consumed by the engine 20. The system of FIG. 1 works well, but better control of the air/fuel ratio is needed.

Thus, there is a need in an evaporative emission control system to provide sensor that monitors both hydrocarbon concentration and flow rate of gas flow in the system to improve an air/fuel ratio of an engine.

SUMMARY

An object of the invention is to fulfill the need referred to above. In accordance with the principles of an embodiment, this objective is achieved an evaporative fuel vapor control system that has a fuel supply for storing fuel that generates fuel vapor in the fuel supply. An internal combustion engine is constructed and arranged to be supplied with fuel from the fuel supply. A vapor canister is in fluid communication with the fuel supply to retain fuel vapor from the fuel supply, and in fluid communication with the engine. Sensor structure includes a body having a sensor portion and an integral tube portion, the tube portion defining a tube having first and second open ends and a passage there-between, one of the ends being fluidly connected with an inlet or an outlet of the canister; a hydrocarbon sensor in the sensor portion and constructed and arranged to determine hydrocarbon concentration of fuel vapor in the tube; a plate having a single, restrictive orifice there-through, the plate being disposed in the tube so that so fuel vapor must pass through the orifice as the fuel vapor moves between the ends of the tube; and pressure transducer structure in the sensor portion and constructed and arranged to determine pressure drop of the fuel vapor across the orifice so as to obtain a flow rate of the fuel vapor through the tube. The system also includes a vapor control valve fluidly connected with an outlet of the canister and disposed between the engine and the canister, and a controller electrically connected with the sensor structure and with the control valve. When the controller receives a signal from the sensor structure indicating the hydrocarbon concentration and the flow rate of the fuel vapor in the tube, the controller is constructed and arranged to cause the control valve to control a flow of the fuel vapor to the engine and to control injection valves that inject fuel into the engine, so that an amount of fuel injected into the engine is based on the determined concentration of hydrocarbons in the fuel vapor.

In accordance with another aspect of an embodiment, a sensor structure for sensing fuel vapor includes a body having a sensor portion and an integral tube portion. The tube portion defines a tube having first and second open ends and a passage there-between. A hydrocarbon sensor is in the sensor portion and is constructed and arranged to determine hydrocarbon concentration of fuel vapor when fuel vapor is in the tube. A plate has a single, restrictive orifice there-through. The plate is disposed in the tube so that so the fuel vapor must pass through the orifice as the fuel vapor moves between the ends of the tube. Pressure transducer structure is in the sensor portion and is constructed and arranged to determine pressure drop of the fuel vapor across the orifice and so as to obtain a flow rate of the fuel vapor through the tube.

In accordance with another aspect of an embodiment, a method controls a ratio of fuel to gas delivered to an internal combustion engine. Fuel for the engine is stored in a fuel supply. The fuel supply generates fuel vapor that is retained in a canister. The canister is in fluid communication with the engine via a flow path. Hydrocarbon concentration of fuel vapor in the flow path is determined. Pressure drop across a restrictive orifice provided in the flow path is measured to determine a flow rate of the fuel vapor in the flow path. A flow of the fuel vapor through the flow path and to the engine is controlled and injection valves that inject fuel into the engine are controlled so that an amount of fuel injected into the engine is based on the determined concentration of hydrocarbons in the fuel vapor.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings, in which.

DETAILED DESCRIPTION OF EXEMPLARY EMBODIMENTS

Figure 1:
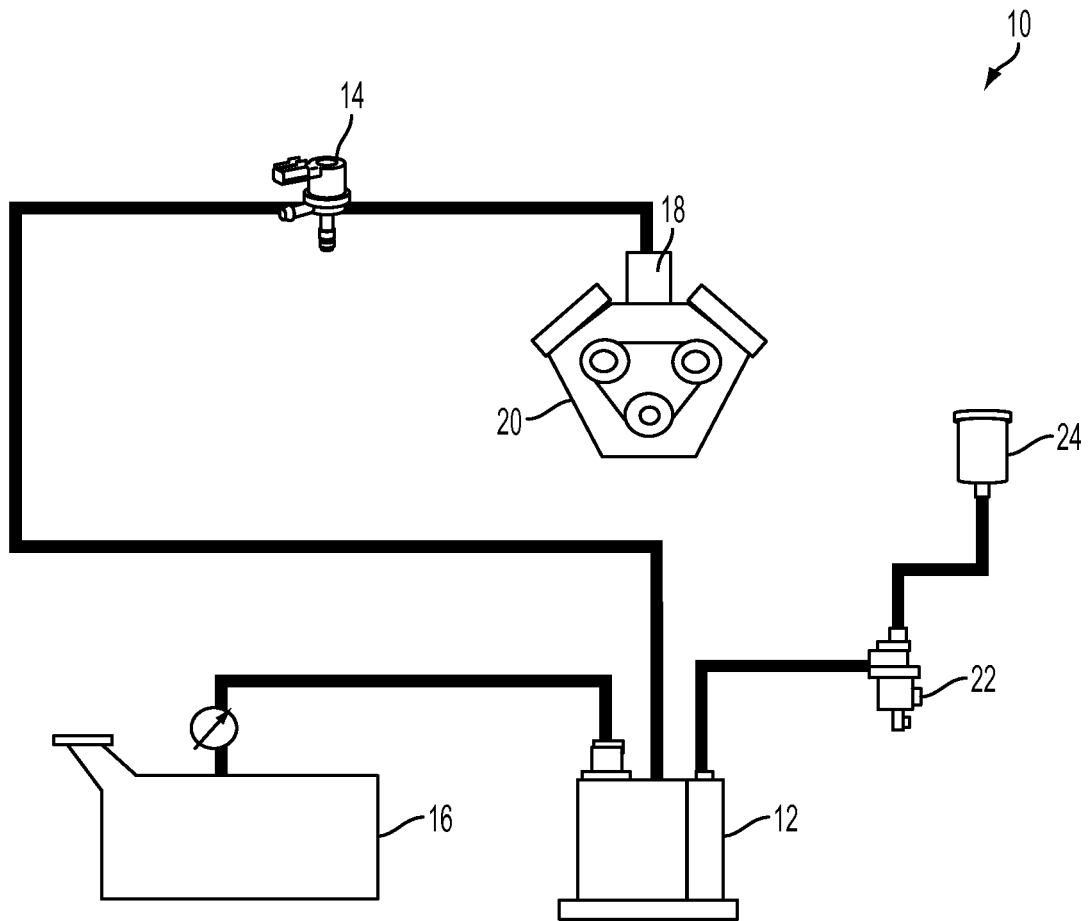
FIG. 1 is a schematic illustration showing a conventional evaporative emission control system.
Figure 2:
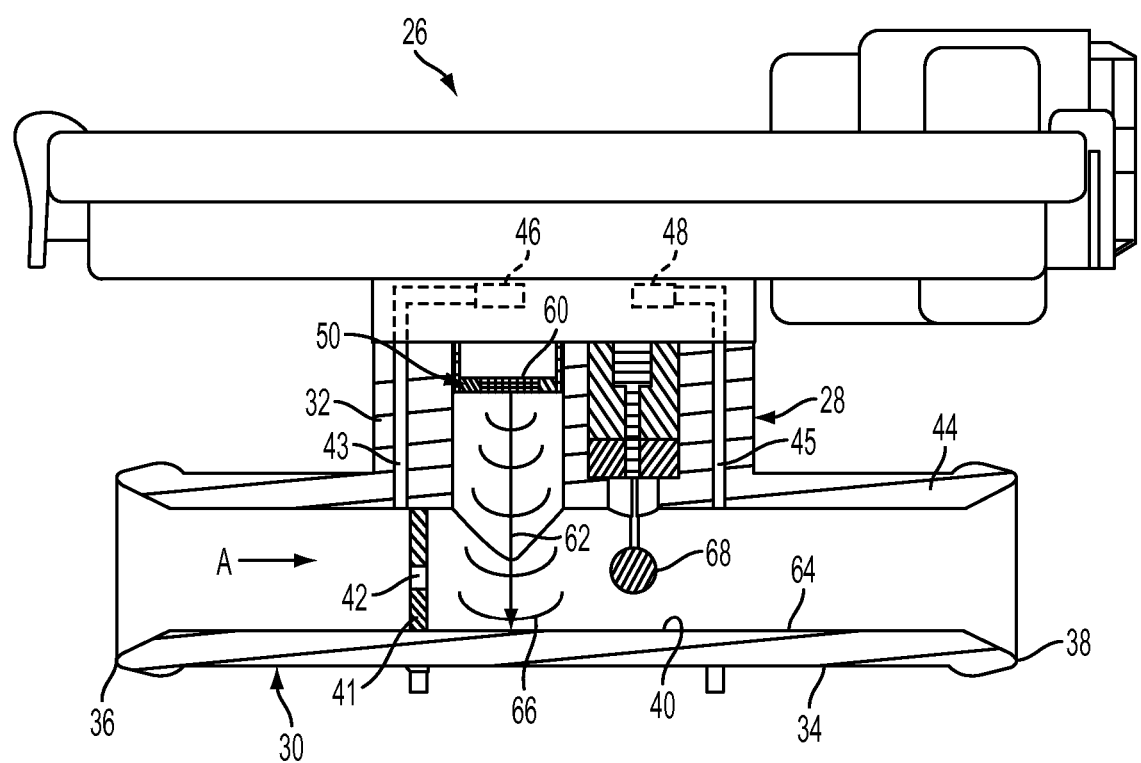
FIG. 2 is a cross-sectional view of single sensor structure for monitoring hydrocarbon concentration and flow rate of gas flow in accordance with an embodiment.

Referring to FIG. 2, a cross-sectional view of sensor structure, generally indicated at 26, for monitoring hydrocarbon concentration and flow rate of fuel vapor flow in an EVAP system is shown in accordance with an embodiment. The sensor structure 26 includes a single housing, generally indicated at 28, that includes a tube portion, generally indicated at 30, and an integral sensor portion 32.

The tube portion 30 defines a tube 34 having opposing open ends 36 and 38, each being constructed and arranged to be mounted to a gas flow line. An interior passage 40 is provided between the ends 36, 38 so that gas can flow through the tube 34. A plate 41 having a single, restrictive orifice 42 therethrough is provided in the tube 34 so that the fuel vapor flow A must pass through the orifice 42 as the flow moves from end 36 to end 38. Pressure drop, as the fuel vapor flow passes through the office 42, is monitored to determine flow rate through the tube 34. In that regard, a first pressure tap port 43 is provided through a wall 44 of the tube 34 and in communication with passage 40, upstream of the orifice 42, and a second pressure tap port 45 is provided through the wall 44 and in communication with the passage 40, downstream of the orifice 42. The tap ports 43 and 45 fluidly communicate with pressure transducer structure that is disposed in the sensor portion 32 of the housing 28. In the embodiment, the pressure transducer structure incudes a high pressure transducer 46 communicating with port 43 and a separate, low pressure transducer 48 communicating with the port 45. The transducer 46 and 48 are disposed in the sensor portion 32 of the housing 28 and can be made integral if desired. Based on the pressure difference across the orifice as measured by the transducers 46 and 48, the flow rate of the fuel vapor flow through the tube 34 can be determined in the conventional manner.

A hydrocarbon sensor, generally indicated at 50 in FIG. 2, is also disposed in the sensor portion 32 of the housing 28. Hydrocarbon sensor 50 is constructed and arranged to measure the concentration of hydrocarbons in fuel vapor flow as explained below.

Figure 3:
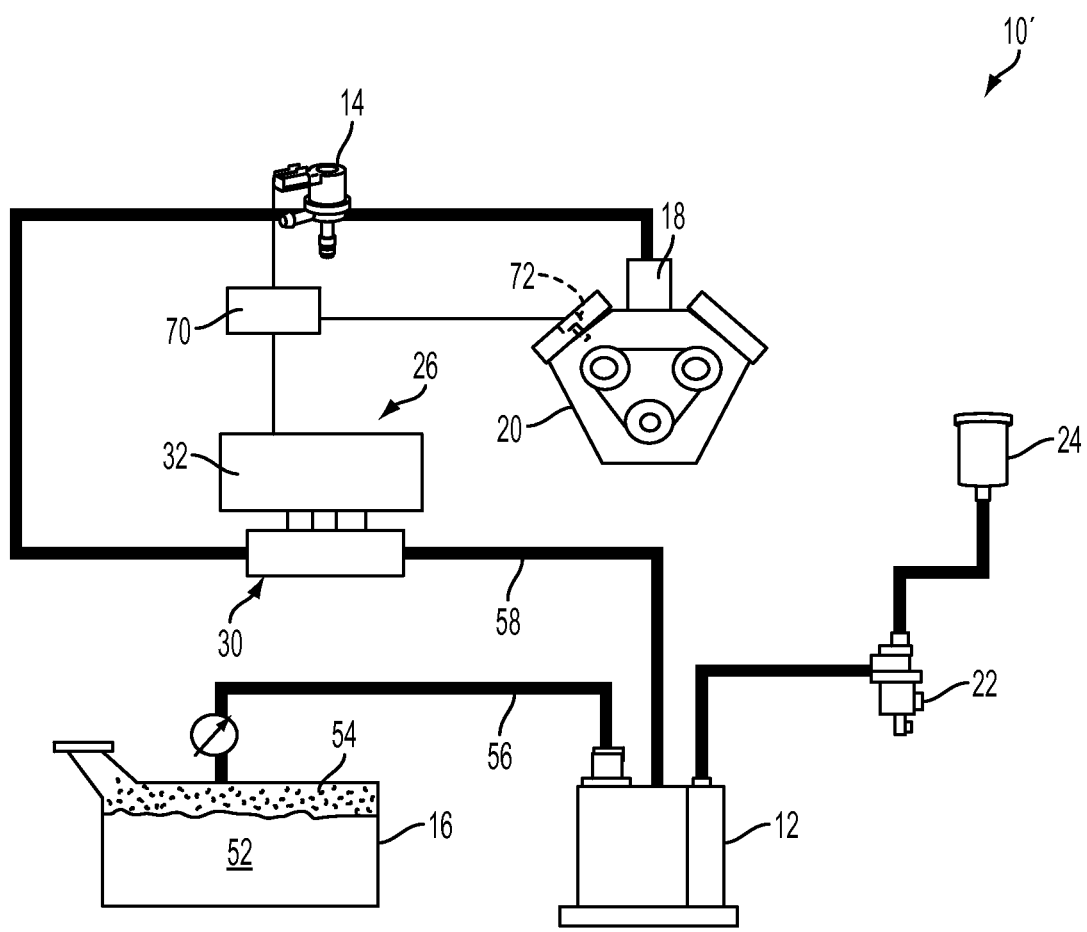
FIG. 3 is a schematic illustration showing an embodiment of an evaporative emission control system employing the sensor structure of FIG. 2 between the canister and purge valve.

With reference to FIG. 3, in the EVAP system 10', liquid fuel 52, such as gasoline, is stored in the fuel tank 16. Fuel vapor 54, including gaseous hydrocarbons 54 such as methane, butane, or propane, which evaporate from the liquid fuel 52, is conducted out of the fuel tank 16 and into the canister 12 via the line 56 which is coupled between the fuel tank 16 and the canister 12. Under certain conditions, the purge valve 14 is opened to direct the fuel vapor 54 through a flow path or line 58 and into the intake manifold 18 to be consumed by the engine 20.

With reference to FIG. 3, in accordance with an embodiment, the sensor structure 26 with the sensor 50 (FIG. 2) and orifice 42 (FIG. 2) is provided in the EVAP system 10', preferably between an outlet of the canister 12 and an inlet of the purge valve 14. In the embodiment, the sensor 50 is an ultrasound transducer constructed and arranged to measure the speed of sound as the fuel vapor flow moves through tube 34.

The hydrocarbon sensor 50 may be of the type disclosed in U.S. Patent Application Publication No. US 2013/0152905, the content of which is hereby incorporated by reference into this specification. With reference to FIG. 2, the tube 34 of the sensor structure 26 is connected in line 58 so as to fluidly connect with the outlet of the canister 12. The hydrocarbon sensor 50 detects a level of hydrocarbons in the tube 34 and thus in line 58 (FIG. 3). The sensor 50 preferably uses ultrasonic sensing technology and has an ultrasound transducer 60 that produces an ultrasonic wave signal 62 that is reflected by the internal wall 64 of the tube 34. The reflected signal 66 is in the range of about 1 mV in amplitude. The single transducer 60 works as a transmitter and receiver. A temperature sensor 68 is provided to account for changing temperature of the fuel vapor flow in tube 34.

The speed of sound in tube 34 depends on temperature and air/gasoline ratio. A signal after-treatment of the transducer 60 measures the runtime of the reflected, acoustic wave signal 66. Since the speed of sound decrease with increasing concentration of hydrocarbons, the main compound being butane, the reflected acoustic wave signal 66 will move more slowly in the tube 34 that is saturated with hydrocarbons (e.g., butane) than in the tube 34 with less hydrocarbon concentration in the fuel vapor flow. The temperature effects of the runtime of the reflected acoustic wave signal 66 are compensated and after recording, the concentration of hydrocarbons is calculated and applied as a linear concentration signal at the output of the sensor structure 26.

By measuring both the flow rate of the fuel vapor flow and the hydrocarbon concentration thereof in line 58, the quantity of energy supplied to the engine 20 in the form of gaseous hydrocarbons is therefore known. Based on this, it is possible to control the air/fuel ratio to the engine 20 in a more efficient manner. This is because less fuel is required to be injected into the engine 20 when more hydrocarbons are supplied to the engine 20 via the intake air.

The hydrocarbon content from the output of sensor 50 and flow rate data from the output of the pressure transducers 46, 48 are sent as signal(s) to an engine controller 70 (FIG. 3) to control injection valves 72 of the internal combustion engine 20 and/or the purge valve 14 in order to control the ratio of fuel to gas in the most efficient manner possible.

The use of the orifice 42 to determine the flow rate of the fuel vapor flow advantageously provides an appropriate sample response time (as compared to using a sonic flow meter), and is cost-effective.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. An evaporative fuel vapor control system comprising:
 a fuel supply for storing fuel that generates fuel vapor in the fuel supply,
 an internal combustion engine constructed and arranged to be supplied with fuel from the fuel supply,
 a vapor canister in fluid communication with the fuel supply to retain fuel vapor from the fuel supply, and in fluid communication with the engine,
 sensor structure comprising:
  a body including a sensor portion and an integral tube portion, the tube portion defining a tube having first and second open ends and a passage there-between, one of the ends being fluidly connected with an inlet or an outlet of the canister,
  a hydrocarbon sensor in the sensor portion and constructed and arranged to determine hydrocarbon concentration of fuel vapor in the tube,
  a plate having a single, restrictive orifice there-through, the plate being disposed in the tube so that so fuel vapor must pass through the orifice as the fuel vapor moves between the ends of the tube, and
  pressure transducer structure in the sensor portion and constructed and arranged to determine pressure drop of the fuel vapor across the orifice so as to obtain a flow rate of the fuel vapor through the tube,
 a vapor control valve fluidly connected with an outlet of the canister and disposed between the engine and the canister, and a controller electrically connected with the sensor structure and with the control valve such that when the controller receives a signal from the sensor structure indicating the hydrocarbon concentration and the flow rate of the fuel vapor in the tube, the controller is constructed and arranged to cause the control valve to control a flow of the fuel vapor to the engine and to control injection valves that inject fuel into the engine, so that an amount of fuel injected into the engine is based on the determined concentration of hydrocarbons in the fuel vapor.

2. The system of claim 1, wherein the sensor structure is mounted between the purge valve and the canister.

3. The system of claim 1, wherein the hydrocarbon sensor is an ultrasonic sensor.

4. The system of claim 2, wherein the hydrocarbon sensor includes an ultrasound transducer constructed and arranged to provide an ultrasonic signal in the passage of the tube and to monitor a runtime of an acoustic wave signal generated by the ultrasonic signal and reflected by the tube.

5. The system of claim 4, wherein the wave signal is constructed and arranged to be about 1 mV in amplitude.

6. The system of claim 1, further comprising a temperature sensor for monitoring a temperature of the fuel vapor in the tube.

7. The system of claim 1, wherein the pressure transducer structure comprises a first pressure transducer constructed and arranged to determine pressure of the fuel vapor upstream of the orifice and a second pressure transducer constructed and arranged to determine pressure of the fuel vapor downstream of the orifice.

8. The system of claim 7, wherein the body includes a first pressure tap port provided through a wall of the tube and in communication with the passage, upstream of the orifice, and a second pressure tap port provided through the wall of the tube and in communication with the passage, downstream of the orifice, the first pressure tap port being in fluid communication with the first pressure transducer, and the second pressure tap port being in fluid communication with the second pressure transducer.

9. A sensor structure for sensing fuel vapor, the sensor structure comprising:

a body including a sensor portion and an integral tube portion, the tube portion defining a tube having first and second open ends and a passage there-between, a hydrocarbon sensor in the sensor portion and constructed and arranged to determine hydrocarbon concentration of fuel vapor when fuel vapor is in the tube, a plate having a single, restrictive orifice there-through, the plate being disposed in the tube so that so the fuel vapor must pass through the orifice as the fuel vapor moves between the ends of the tube, and pressure transducer structure in the sensor portion and constructed and arranged to determine pressure drop of the fuel vapor across the orifice so as to obtain a flow rate of the fuel vapor through the tube.

10. The sensor structure of claim 9, wherein the hydrocarbon sensor is an ultrasonic sensor.

11. The sensor structure of claim 9, wherein the hydrocarbon sensor includes an ultrasound transducer constructed and arranged to provide an ultrasonic signal in the passage of the tube and to monitor a runtime of an acoustic wave signal generated by the ultrasonic signal and reflected by the tube.

12. The sensor structure of claim 11, wherein the wave signal is constructed and arranged to be about 1 mV in amplitude.

13. The sensor structure of claim 9, further comprising a temperature sensor constructed and arranged to monitor a temperature of the fuel vapor when in the tube.

14. The sensor structure of claim 9, wherein the pressure transducer structure comprises a first pressure transducer constructed and arranged to determine pressure of the fuel vapor upstream of the orifice and a second pressure transducer constructed and arranged to determine pressure of the fuel vapor downstream of the orifice.

15. The sensor structure of claim 14, wherein the body includes a first pressure tap port provided through a wall of the tube and in communication with the passage, upstream of the orifice, and a second pressure tap port provided through the wall of the tube and in communication with the passage, downstream of the orifice, the first pressure tap port being in fluid communication with the first pressure transducer, and the second pressure tap port being in fluid communication with the second pressure transducer.

* * * * *